(12) United States Patent
Högberg et al.

(10) Patent No.: US 6,740,239 B2
(45) Date of Patent: May 25, 2004

(54) METHOD AND APPARATUS FOR PROCESSING BLOOD AND BLOOD COMPONENTS

(75) Inventors: Niclas Högberg, Karlskoga (SE); Emanuel Hällgren, Karlskoga (SE); Peter Pihlstedt, Stockholm (SE)

(73) Assignee: Gambro, Inc., Lakewood, CO (US)

( * ) Notice: Subject to any disclaimer, the term of this patent is extended or adjusted under 35 U.S.C. 154(b) by 235 days.

(21) Appl. No.: 10/000,464

(22) Filed: Nov. 30, 2001

(65) Prior Publication Data

US 2002/0119880 A1 Aug. 29, 2002

(30) Foreign Application Priority Data

Oct. 26, 1999 (SE) ................................................ 9903841

(51) Int. Cl.⁷ ............................................... B01D 11/00
(52) U.S. Cl. ................. 210/634; 210/198.1; 210/512.1; 210/787; 494/27; 604/410
(58) Field of Search ................................. 210/143, 145, 210/198.1, 360.1, 380.1, 512.1, 634, 782, 787, 789; 422/72, 101; 436/177, 178; 494/5, 16, 17, 23, 27, 30, 37, 45, 21

(56) References Cited

U.S. PATENT DOCUMENTS

| | | |
|---|---|---|
| 3,096,283 A | 7/1963 | Hein |
| 3,145,713 A | 8/1964 | Latham, Jr. |
| 3,244,363 A | 4/1966 | Hein |
| 3,326,458 A | 6/1967 | Meryman et al. |
| 3,329,136 A | 7/1967 | Cadlou |
| 3,456,875 A | 7/1969 | Hein |
| 3,489,145 A | 1/1970 | Judson et al. |
| 3,519,201 A | 7/1970 | Eisel et al. |
| 3,600,900 A | 8/1971 | Buddecke |
| 3,679,128 A | 7/1972 | Unger et al. |

(List continued on next page.)

FOREIGN PATENT DOCUMENTS

| | | |
|---|---|---|
| DE | 38 15 645 | 11/1989 |
| EP | 0 304 431 | 3/1989 |
| EP | 0 508 474 A2 A3 | 10/1992 |
| EP | 0 578 086 | 1/1994 |
| EP | 0 935 966 | 8/1999 |
| FR | 84 11225 | 1/1986 |
| GB | 1373672 | 11/1974 |
| SE | 354 581 | 3/1973 |
| SE | 354 582 | 3/1973 |
| WO | 85/02561 | 6/1985 |
| WO | 87/06844 | 11/1987 |

(List continued on next page.)

OTHER PUBLICATIONS

A.H. Runck et al., *Continuous–flow Centrifugation Washing of Red Blood Cells*, Transfusion, vol. 12, No.4, Jul.–Aug. 1972, pp. 237–244.

T.J. Contreras et al., *A Comparison of Methods to Liquid–Stored Red Blood Cells and Red Blood Cells Frozen with High or Low Concentrations of Glycerol*, Transfusion, vol. 16, No. 6, Nov. –Dec. 1976, pp. 539–565.

*Primary Examiner*—Joseph Drodge
(74) *Attorney, Agent, or Firm*—Edna M O'Connor; John R. Merkling; Laura M. Butterfield

(57) ABSTRACT

The claimed invention relates to a method and a device for processing blood concentrate products before they are exposed to a continued process for extracting those remaining medicinally interesting sub-components. The appropriate pre-processing, in relation to the invention, primarily entails a mechanically powered resolution of the viscous flowing concentrate products in a diluting solution for the adaptation of the total products for a renewed centrifuging. The device includes a centrifuge machine containing one or more suspended product bags that can be oscillated forwards and backwards in an incomplete pendulum swing by operation of a motor mounted in a lid of the machine. The product bag(s) are connected to a ring bag for subsequent processing and to a bag containing diluting solution by a multi-way connector.

19 Claims, 2 Drawing Sheets

U.S. PATENT DOCUMENTS

| | | | |
|---|---|---|---|
| 3,708,110 A | 1/1973 | Unger et al. | |
| 3,724,747 A | 4/1973 | Unger et al. | |
| 3,737,096 A | 6/1973 | Jones et al. | |
| 3,858,796 A | 1/1975 | Unger et al. | |
| 3,864,089 A | 2/1975 | Tiffany et al. | |
| 3,885,735 A | 5/1975 | Westbert | |
| 3,987,961 A | 10/1976 | Sinn et al. | |
| 4,010,894 A | 3/1977 | Kellogg et al. | |
| 4,016,828 A | 4/1977 | Maher, Jr. et al. | |
| 4,018,911 A * | 4/1977 | Lionetti et al. | |
| 4,111,355 A | 9/1978 | Ishimaru | |
| 4,131,369 A | 12/1978 | Gordon et al. | |
| 4,132,439 A | 1/1979 | Millar | |
| 4,142,670 A | 3/1979 | Ishimaru et al. | |
| 4,230,263 A | 10/1980 | Westberg | |
| 4,244,513 A | 1/1981 | Fayer et al. | |
| 4,268,393 A | 5/1981 | Persidsky et al. | |
| 4,278,202 A | 7/1981 | Westberg | |
| 4,303,193 A | 12/1981 | Latham, Jr. | |
| 4,304,357 A | 12/1981 | Schoendorfer | |
| 4,386,730 A | 6/1983 | Mulzet | |
| 4,387,848 A | 6/1983 | Kellogg et al. | |
| 4,388,184 A | 6/1983 | Brous et al. | |
| 4,389,206 A | 6/1983 | Bacehowski et al. | |
| 4,389,207 A | 6/1983 | Bacehowski et al. | |
| 4,405,079 A | 9/1983 | Schoendorfer | |
| 4,419,089 A | 12/1983 | Kolobow et al. | |
| 4,421,503 A | 12/1983 | Latham, Jr. et al. | |
| 4,439,177 A | 3/1984 | Conway | |
| 4,447,221 A | 5/1984 | Mulzet | |
| 4,459,169 A | 7/1984 | Bacehowski et al. | |
| 4,482,342 A | 11/1984 | Lueptow et al. | |
| 4,530,691 A | 7/1985 | Brown | |
| 4,617,009 A | 10/1986 | Öhlin et al. | |
| 4,720,284 A | 1/1988 | McCarty | |
| 4,767,397 A | 8/1988 | Hohenberg et al. | |
| 4,846,780 A | 7/1989 | Galloway et al. | |
| 4,850,952 A | 7/1989 | Figdor et al. | |
| 4,925,442 A | 5/1990 | Bodelson | |
| 4,934,995 A | 6/1990 | Cullis | |
| 4,936,820 A | 6/1990 | Dennehey et al. | |
| 4,940,543 A | 7/1990 | Brown et al. | |
| 4,990,132 A | 2/1991 | Unger et al. | |
| 5,006,103 A | 4/1991 | Bacehowski et al. | |
| 5,032,288 A | 7/1991 | Columbus et al. | |
| 5,114,396 A | 5/1992 | Unger et al. | |
| 5,160,310 A | 11/1992 | Yhland | |
| 5,217,426 A | 6/1993 | Bacehowski et al. | |
| 5,217,427 A | 6/1993 | Cullis | |
| 5,316,540 A | 5/1994 | McMannis et al. | |
| 5,571,068 A | 11/1996 | Bacehowski et al. | |
| 5,593,378 A | 1/1997 | Dyck | |
| 5,610,074 A * | 3/1997 | Beritashvili et al. | 436/177 |
| 5,651,766 A | 7/1997 | Kingsley et al. | |
| 5,674,173 A | 10/1997 | Hlavinka et al. | |
| 5,704,887 A | 1/1998 | Slowik et al. | |
| 5,723,050 A | 3/1998 | Unger et al. | |
| 5,733,253 A | 3/1998 | Headley et al. | |
| 5,759,147 A | 6/1998 | Bacehowski et al. | |
| 5,789,259 A * | 8/1998 | Wardlaw | 436/177 |
| 6,261,217 B1 | 7/2001 | Unger et al. | |
| 6,315,706 B1 | 11/2001 | Unger et al. | |
| 6,348,031 B1 | 2/2002 | Unger et al. | |

FOREIGN PATENT DOCUMENTS

| | | |
|---|---|---|
| WO | 87/06857 | 11/1987 |
| WO | 89/02273 | 3/1989 |
| WO | 92/00145 | 1/1992 |
| WO | 94/25086 | 11/1994 |
| WO | 95/01842 | 1/1995 |
| WO | 95/04591 | 2/1995 |
| WO | 96/29081 | 9/1996 |
| WO | 98/35757 | 8/1998 |
| WO | 98/46362 | 10/1998 |
| WO | 01/02037 | 1/2001 |

* cited by examiner

METHOD AND APPARATUS FOR PROCESSING BLOOD AND BLOOD COMPONENTS

This application claims the benefit of International PCT Application No. PCT/SE00/01077 filed 26 May 2000, which claims priority from Swedish Patent Application No. 9903841-6 filed 26 Oct. 1999.

BACKGROUND OF THE INVENTION

The claimed invention relates to a method and an apparatus for pre-processing blood concentrate products before they are exposed to continued processing for extracting those remaining subcomponents that are of interest. The pre-processing of blood concentrate products, primarily pertaining to the invention, entails a resolution of these in a diluting solution and a flushing of the containers or bags in which the blood concentrate products are delivered. This makes possible the following processing operation in the form of centrifuging and the dividing up of blood concentrate products into blood-platelet plasma and waste products.

The invention is primarily intended for pre-processing of such blood concentrate products that are designated "Buffy Coat" at blood-donor centres and which are obtained from red blood cells and plasma from whole blood and which at present are utilised for extracting valuable medicinal blood-platelet plasma. At this stage the Buffy Coat is a thick viscous liquid that must be resolved in a suitable diluting solution before it can be exposed to renewed centrifuging. An example of such a standardised diluting solution, which is widely used, is generally designated T-Sol. In normal cases the Buffy coat is accessible in the form of concentrate from the previous extraction of red blood cells and plasma from whole blood. Each concentrate batch of Buff, Coat is, as a rule, too small to be worth an individual centrifuging after resolution in the current diluting solution. As every Buffy Coat concentrate is initially accessible in its own blood processing bag, a decided amount of diluting solution was previously added manually to each one of a certain amount of blood processing bags and shaken manually until an acceptable mixing had taken place, followed by emptying them together into a larger bag which was then centrifuged.

Apart from the manual handling and the time required for this there is also the added risk to the person who must shake the blood bags and in the long term can receive injury to the neck and shoulders.

SUMMARY OF THE INVENTION

To be able to also automate this stage in blood processing it is suggested, in accordance with the claimed invention, the use of a specially intended set of bags preferably containing a ring-shaped bag for the following centrifuging operation as well as the use of a characteristic automatic mixing device, special to the invention, in which the Buffy coat is added and resolved in a diluting solution. In the design of this part of the invention, preferred, by us the mixing function or the mixing device has been built into or made connectable to the outer lid of the centrifuge that is utilised in the processing stage that follows after. Nevertheless, the device can also be made to stand completely by itself without changing the original concept. In the device, in accordance with the invention, a smaller electrically driven motor is thus included which, when the device is combined with the centrifuge, is secured to the lid of the centrifuge. This motor has the distinct feature of never doing a complete revolution in any direction but is quickly stopped before a revolution is completed then followed by an incomplete revolution in the opposite direction. A movement of approximately one of quarter revolution (such as +92°), at the most lasting several minutes, has shown that it gives the desired mixing function, which, as shown as follows, has, as its task the replacement of the prior manual resolution of the Buffy Coat and the flushing out of the Buffy Coat bags with the required amount of diluting solution, which, today was generally preceded by Pooling, in other words, the merging of several flushed out quantities of concentrate products to form a mass that is suitable for centrifuging. The device's special movement pattern can be attained with a gear box, a crank function or via the control of its motor. In theory, a hydraulic motor could also be used for this purpose although a longer shaking rate and a longer mixing time should be taken into account. Connected to the aforementioned motor there is a cassette or holder in which the number of concentrate bags with Buffy Coat intended to be included in a process can be connected. Before the concentrate bags are connected to the cassette they have been individually connected by sterile welding to individual connecting tubes then to the bag set intended for processing, which, in turn, leads to a connecting tube with which all bags containing Buffy Coat can be joined to a bag with the required amount of diluting solution, as well as via a second connecting tube to the ring bag intended for finishing centrifuging and finally to a connecting tube between the ring bag and a storage bag for the desired final product. Together these components make up a functionally sealed system which is easy to handle and completely protected against external bacteria, etc.

When extracting blood platelet plasma from the Buff coat the number of bags with the original material that are intended for centrifuging are connected to individual connecting tubes in the aforementioned bag set. These connecting tubes are then connected, each in turn, to a multi-way connector to which the connecting tube form the diluting solution bag is also connected. A clamp valve is applied to the latter connecting tube while the bags with Buffy Coat are secured to the aforementioned cassette and the bag with the diluting solution is suspended in the intended holder sufficiently high up to allow the desired amount of diluting solution to be transferred to each respective Buffy Coat bag. The addition of the diluting solution to the Buffy Coat bags is then controlled by the clamp valve, which, in turn, is controlled by a control program that can be included in the control program of the control system of the centrifuge, which also selects the time to start the motor and the time it must be operated. Appropriately, the diluting solution is added in several portions with a motor driven action between each addition. Dissolving the Buffy Coat in the diluting solution is thus carried out without any manual shaking operation. Due to the special timed movement, back and forth, of the motor the problem of damaging the different tubes is avoid. It is only the ring bag and the tube between it and the final product's storage bag that are affected by the mixing operation. After the dissolution of the Buffy Coat in the different exit bags is finalised the content of all bags are added to the bag set included in the ring bag via a separate connecting tube, which also is connected to the previously named multi-way connector and which on its way to the ring bag is placed in a clamp valve by which this connection is controlled. After all substance has been transferred to the ring bag the connection is interrupted between the ring bag and the exit bags and the diluting solution bag, the appropriate connecting tube is removed by welding from the centrifuge rotor support which it passes, after which the empty bags and their connecting tubes can be rejected.

Following this the diluting solution/Buffy Coat mix is centrifuged while the bag intended for storing the end product is located in the centre chamber of the centrifuge rotor. After centrifuging the lighter blood platelet product is transferred to the final storage bag. The designed device is utilised in a known way to expose the ring bag to an outer pressure thus emptying it to a greater or lesser degree. This device consists of a membrane arranged under the ring bag under which hydraulic fluid can be added and therefore expose the ring bag to an external pressure. When emptying the ring bag must be interrupted it is determined by one or more photocells in the outer lid of the centrifuge, which utilise the difference in colour between the light desired bloodplatelet's end product and those dark heavy concentrate products that are gathered along the outer periphery. When emptying the ring bag it is suitable to do it via the already described cell trap, which can, for example, be one of the types, described in WO 97/30715. After the desired amount of blood-plateiet plasma has been removed from the ring bag the connecting tube between the ring bag and final storage bag is welded in a known way and thereby blocking the ends of both tubes. All that remains after that is to point out that the holder for the diluting solution bag and cassette for the Buffy Coat bags can be made removable in order not to interfere with the other functions of the centrifuge.

BRIEF DESCRIPTION OF THE DRAWINGS

The invention in its various functions has now been defined in the subsequent patent claims and they shall now only be somewhat more described in relation to the attached figures.

Of these

DETAILED DESCRIPTION OF THE INVENTION

Figure 1:
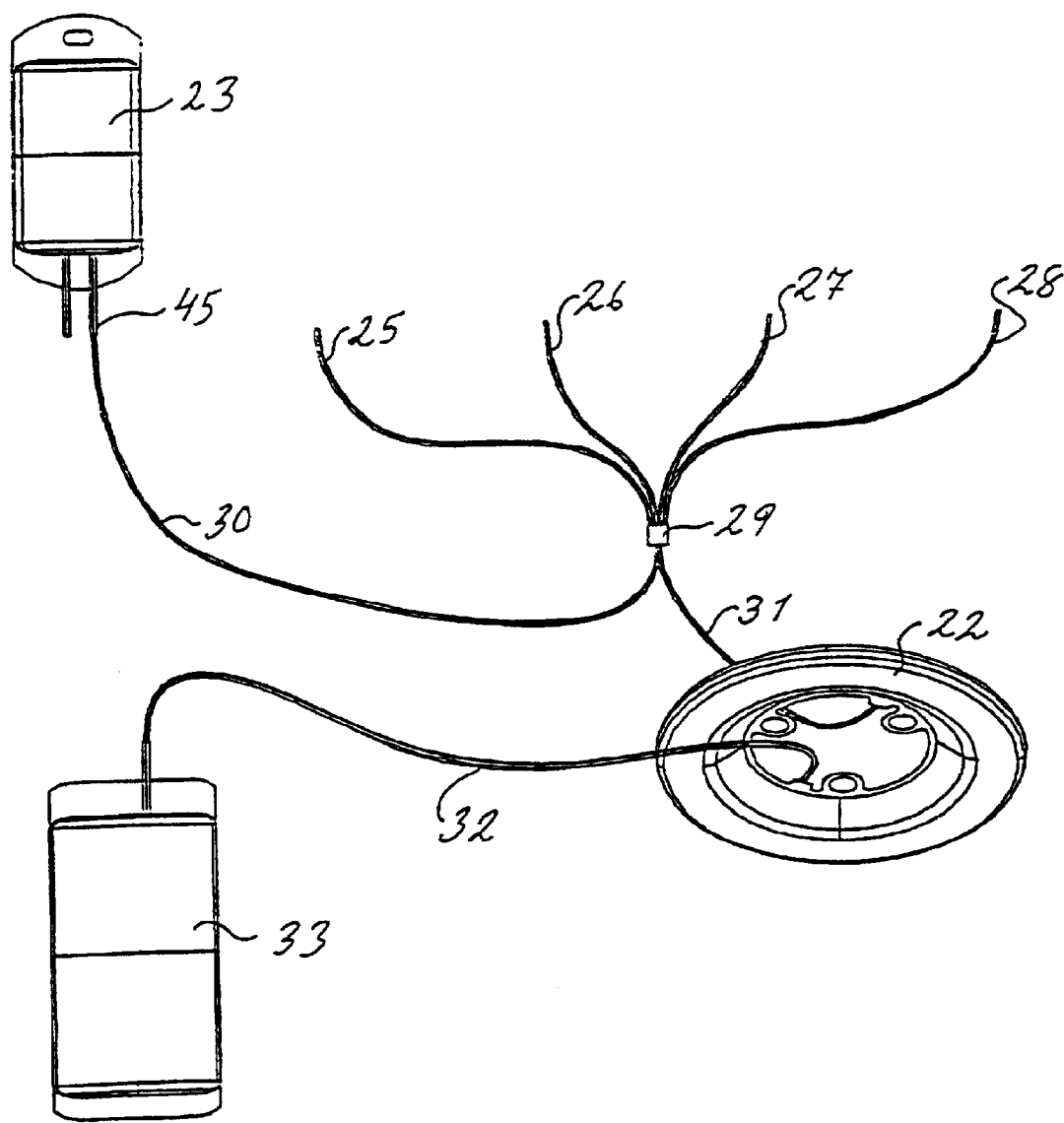
FIG. 1 a bag set intended for blood-platelet production from Buffy Coat.

The bag shown in FIG. 1 for blood-platelet production from Buffy Coat comprises ring bag 22, a bag for diluting solution 23, four connecting tubes 25–28 (the number of connecting tubes can vary but should as a rule be between 4 and 6), each one is intended for welding to one bag of Buffy Coat, a multi-way connector 29 which, on the one hand, is connected via tube 30 to the diluting solution bag 23 and, on the other hand, to another tube 31 to ring bag 22. From the latter there is one more tube 32 that finally goes to final storage bag 33. In tube 30 connecting to diluting solution 23 there is a breaker switch 45, which, when required to add the diluting solution to tubes 25–28, which are connected to the bags with Buffy Coat, can be opened by sharply bending the tube. Before the breaker switch is opened the connecting tube 30 must be engaged in guide groove 12 in one of the supports 9–11 with which the clamp valve function is intended to control the added diluting solution.

Figure 2:
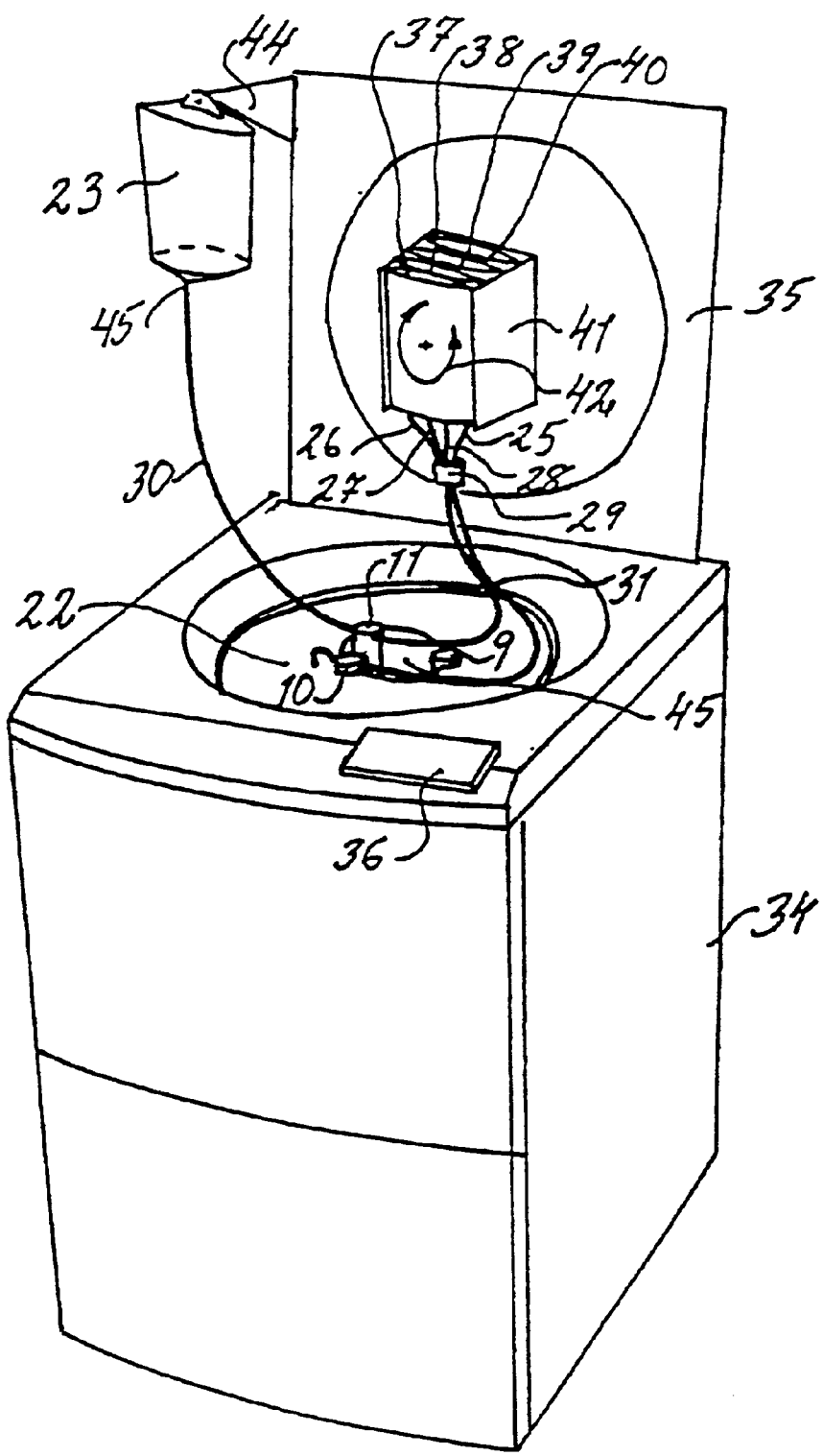
FIG. 2 angle projection of the equipped centrifuge in accordance with the invention for autopooling.

As the bag set shown in FIG. 1 is the same as illustrated in FIG. 2 we have retained the same notations although the parts are drawn to a smaller scale and consequently also with fewer parts. Otherwise, in FIG. 2 centrifuge 34 is shown standing with its outer lid 35 completely open and locked in position. The inner lid of the centrifuge has not been taken into account in the figure as it made the figure unclear when drawn in position. Also the centrifuge rotor and ring bag 22 has been drawn, to a certain extent, in a simplified way. The control panel of the centrifuge is numbered 36 in the figure. Furthermore, the figure shows a position with four blood bags of Buffy Coat 37–40 suspended in a cassette 41, which is mounted on the outer lid of the centrifuge. The respective outlets of blood bags 37–40 have, by sterile welding, been connected to tube connectors 25–28 and the fluid content of the bags has been transferred to ring bag 22 via these tubes and connecting tube 31. After that, bags 37–40 have received cleaning and diluting fluid from the diluting fluid bag 23 suspended in holder 44. Diluting fluid bag 23 is suspended sufficiently high above bags 37–40 to enable the diluting solution, in sufficient amounts, to be added to the bags as soon as breaker switch 45 in tube 30 and clamp valve in support 11, which tube 30 passes, is opened. Communication between bags 37–40 and ring bag 22 is via tube 31 which, in turn, passes clamp valve in support 10 by which communication is controlled. As the addition of diluting solution in sufficient amounts to the bags 37–40 starts with the cassette connected motor (not seen on the figure) that operates cassette 41 forwards and backwards in a pendulum movement, in accordance with curve 42, until all the concentrate substance in the Buffy Coat bags has dissolved, after which the built-in clamp valve on support 10 opens up, which outlet tube 31 from multi-way connector 29 passes through and all substance is added to ring bag 22 after which tube 31, in support 10 is sterile welded and blocked whereby the empty bags 37–40 and bag 23 with the concentrate from the diluting solution can be rejected together with the tube system. Flushing out of the blood bags can, if, necessary be carried out as two or several consecutive flushing stages. After the prepared flushing of the blood bags cassette 41 and holder 44 are removed from the centrifuge lid the centrifuge is closed and centrifuging is carried out. Final storage bag 33 is located in centre chamber 45 of the centrifuge. After centrifuging all blood-platelet plasma is transferred to final storage bag 33 via location 5, under the ring bag, being supplied by hydraulic fluid which exposes the bag to an outer pressure which clamps it together. Emptying the ring bag is interrupted by photocell 52 when it registers that the interface between the desired lighter substance and the darker non-desired concentrate product starts to reach the outlet via tube 32. Following this, tube 32 is sterile welded and sealed in one of the supports 9–11, after which the ring bag with the non-desired concentrates of red blood cells, etc. can be rejected.

What is claimed is:

1. A method for processing a blood concentrate product for separating a medicinally valuable blood component comprising: connecting at least one product bag containing a blood concentrate product to be proceased with a tube system having a plurality of tubes connected to a multi-way connector and connecting also a solution bag containing a diluting solution via a solution tube to the tube system in communication with the multi-way connector, suspending the at least one product bag containing the blood concentrate product to be processed in a cassette, processing the blood concentrate product in the at least one product bag by oscillating the cassette forwards and backwards in an incomplete pendulum swing, adding the diluting solution from the solution bag through the tube system in an adapted portion to each of the at least one product bags, keeping the cassette in motion until all blood concentrate products are dissolved in the added diluting solution, and transferring the contents of all of the at least one product bags in the cassette to a ring bag for a subsequent centrifugation processing step.

2. A method in accordance with claim 1 whereby the amount of diluting solution added to the at least one product bag is controlled by a clamp valve through which the solution tube is passed and which clamp valve optionally utilized when processing is finalized to weld the solution tube.

3. A method in accordance with claim 1 whereby the pendulum movement of the cassette is held within approximately a quarter revolution in either the forward or backward direction.

4. A method in accordance with claim 1 whereby the step of transferring to the ring bag the contents of all of the at least one product bags containing a blood concentrate product occurs after the steps of adding and processing.

5. A method in accordance with claim 1 in which the step of adding the diluting solution and the step of transferring the concentrate products takes place in several steps with mixing as the middle step.

6. A method in accordance with claim 1, in which the steps of oscillating the cassette and adding diluting solution occur at least partially at the same time.

7. A method in accordance with claim 1, whereby the connecting step comprises connecting a plurality of blood product bags each containing a blood concentrate product to be processed; and whereby said step of adding a diluting solution includes adding diluting solution to each of the plurality of product bags.

8. A method in accordance with claim 7, whereby said step of adding a diluting solution includes flowing the diluting solution to each of the plurality of product bags through the multi-way connector.

9. A method in accordance with claim 9, whereby the step of transferring includes transferring the contents of each of the plurality of product bags to the ring bag.

10. A method in accordance with claim 9 whereby said step of transferring includes flowing the contents of each of the plurality of product bags to the ring bag through the multi-way connector.

11. A method in accordance with claim 1 which further comprises a step for removing a processed blood component from the ring bag after the subsequent centrifugation processing step.

12. A bag set for processing blood concentrate products comprising a ring bag, a processed component bag connected to the ring bag, a multi-way connector connected to the ring bag, one or more connecting tubes that are adapted to be individually connected to one or more discrete sources of blood concentrate products, said one or more connecting tubes also being connected to the multi-way connector and a diluting solution tube connected to the multi-way connector, the diluting solution tube being adapted to be connected to a discrete source of diluting solution, said multiway connector selectively connecting the one or more connecting tubes and the diluting solution tube or the one or more connecting tubes and the ring bag whereby the source of diluting solution can be connected with each discrete source of blood products placing diluting solution in fluid communication with said blood products, and whereby each discrete source of blood products can be connected with the ring bag, emptying said blood products and diluting solution from said discrete sources of blood concentrate products into said ring bag, while the processed component bag is separately connected to the ring bag.

13. A device for processing a blood concentrate product comprising a centrifuge machine to which is connected a cassette in which a plurality of product bags containing blood concentrate products to be processed are suspended and having means for putting the cassette in motion in a forward and backward pendulum movement in an incomplete revolution about the axis and said means comprising an outer lid which has a motor disposed therein which operates in an incomplete revolution in one direction immediately followed by a corresponding incomplete return revolution in the other direction, said motor being operably connected to the cassette such that when the outer lid of the centrifuge is in an open position, a plurality of product bags can be suspended in the cassette, so that when the motor is activated the product bags are exposed to a mechanical mixing of the blood concentrate products disposed therein.

14. A device in accordance with claim 13 in which the centrifuge machine further has attached thereto an instrument for holding a bag containing a diluting solution.

15. A device in accordance with claim 13 whereby the pendulum movement of the cassette is maintained within the interval of approximately a quarter revolution forward and backward.

16. A device for processing a blood concentrate product in accordance with claim 13, which further comprises a clamp valve through which a diluting solution tube may be passed whereby the diluting solution tube is connected between a diluting solution bag and the plurality of blood product bags, and whereby an amount of diluting solution is added to the plurality of product bags, the amount of diluting solution being controlled by the clamp valve.

17. A device for processing a blood concentrate product in accordance with claim 16, whereby the clamp valve is adapted to also be utilized when processing is finalized to weld the diluting solution tube.

18. A device for processing a blood concentrate product in accordance with claim 16, which further comprises a support which has a controllable clamp and a welding station which can be actuated to block or weld a diluting solution tube adapted to be disposed therein.

19. A device for processing a blood concentrate product in accordance with claim 16, which further comprises a second clamp valve to control the flow of processed blood concentrate product from the plurality of product bags to a ring bag via a tube connecting the product bags to the ring bag.

* * * * *